(12) United States Patent
Ben-David et al.

(10) Patent No.: US 11,191,959 B2
(45) Date of Patent: Dec. 7, 2021

(54) MONITORING AND TREATMENT SYSTEM FOR NEUROLOGICAL DISORDERS

(71) Applicant: COGNIGUARD MEDICAL HOLDINGS LIMITED, Nicosia (CY)

(72) Inventors: Tamir Ben-David, Tel Aviv (IL); Nimrod Kadim, Modi'in (IL); Shmuel Glasberg, Herzeliya (IL); Ra'anan Gefen, Re'ut (IL)

(73) Assignee: COGNIGUARD MEDICAL HOLDINGS LIMITED, Nicosia (CY)

( * ) Notice: Subject to any disclaimer, the term of this patent is extended or adjusted under 35 U.S.C. 154(b) by 187 days.

(21) Appl. No.: 16/468,367

(22) PCT Filed: Dec. 11, 2017

(86) PCT No.: PCT/IB2017/057780
§ 371 (c)(1),
(2) Date: Jun. 11, 2019

(87) PCT Pub. No.: WO2018/109633
PCT Pub. Date: Jun. 21, 2018

(65) Prior Publication Data
US 2021/0128916 A1 May 6, 2021

Related U.S. Application Data

(60) Provisional application No. 62/432,843, filed on Dec. 12, 2016.

(51) Int. Cl.
*A61N 1/36* (2006.01)
*A61N 1/04* (2006.01)
*A61N 1/05* (2006.01)

(52) U.S. Cl.
CPC ....... *A61N 1/36025* (2013.01); *A61N 1/0452* (2013.01); *A61N 1/0456* (2013.01);
(Continued)

(58) Field of Classification Search
CPC ............ A61N 1/36025; A61N 1/36031; A61N 1/0456; A61N 1/0541; A61N 1/0452; A61N 1/0472
(Continued)

(56) References Cited

U.S. PATENT DOCUMENTS

2002/0002390 A1  1/2002  Fischell et al.
2003/0195588 A1  10/2003  Fischell et al.
(Continued)

*Primary Examiner* — Amanda K Hulbert
*Assistant Examiner* — Philip C Edwards
(74) *Attorney, Agent, or Firm* — JMB Davis Ben-David (57) ABSTRACT

The invention provides a system for inhibition or treatment of an aberrant neurological event in a subject. The system comprises: one or more detectors; a controller; and one or more stimulators of the vagus nerve. The invention also provides a method for treating and preventing epileptic seizures and the onset or pre-onset of epileptic seizures. The method includes the steps of: collecting signals from each of one or more detector indicating the presence of a repetitive movement; analyzing signals received from the one or more detector to determine the intensity of the stimulation of the auricular branch of the vagus nerve (ABVN) required to control, moderate or prevent current and future repetitive movements; and when required, signaling one or more stimulator to stimulate the ABVN so that the repetitive motion ceases using the determined stimulation intensities.

23 Claims, 3 Drawing Sheets

(52) U.S. Cl.
CPC ......... *A61N 1/0472* (2013.01); *A61N 1/0541* (2013.01); *A61N 1/36031* (2017.08)

(58) Field of Classification Search
USPC .......................................................... 607/62
See application file for complete search history.

(56) References Cited

U.S. PATENT DOCUMENTS

| | | | |
|---|---|---|---|
| 2010/0198282 A1 | 8/2010 | Rogers et al. | |
| 2012/0035680 A1* | 2/2012 | Napadow | A61B 5/113 |
| | | | 607/17 |
| 2013/0066395 A1* | 3/2013 | Simon | A61B 5/4094 |
| | | | 607/48 |

\* cited by examiner

Fig. 1- general closed loop stimulation system description

Fig. 2 – closed loop stimulation system, remote control and remote monitoring

MONITORING AND TREATMENT SYSTEM FOR NEUROLOGICAL DISORDERS

CROSS-REFERENCE TO RELATED APPLICATIONS

This is the U.S. National Stage of International Patent Application No. PCT/IB2017/057780 filed Dec. 11, 2017, which was published in English under PCT Article 21(2), and which in turn claims the benefit of U.S. Provisional Patent Application No. 62/432,843 filed Dec. 12, 2016.

FIELD

This disclosure relates to a system for monitoring and treatment of neurological disorders, particularly those often expressed in aberrant muscular behavior.

BACKGROUND

Epilepsy is a neurological disorder involving recurrent seizures. A seizure, also sometimes called a convulsion, is a sudden change in behavior caused by increased electrical activity in the brain.

There is an inherent relationship between sleep and epilepsy. Sleep activates the electrical charges in the brain that result in seizures and seizures are timed according to the sleep-wake cycle. For some people, seizures occur exclusively during sleep. It was found that up to 45% of people with epilepsy have seizures that occur predominantly or exclusively during sleep or occur with sleep deprivation. Epileptic episodes during sleep may have severe results as the person undergoing the seizure is usually alone at night.

Children with epilepsy must cope with a variety of problems as a result of their disorder that goes beyond seizure control. Sleep problems are among the most critical. It was found that parents of children with epilepsy sleep 4 hours per night on average and that they wake up an average of 3 times per night to check on their children.

A person may experience a brief episode of a neurological disorders which typically isn't expressed in aberrant muscular behavior. However, neurological disorders which are expressed in aberrant muscular behavior, spasms, or seizures tend to be longer than one second, for example ten seconds.

One of the more effective non-medical treatments for epilepsy is vagal nerve stimulation (VNS) that prevents seizures by sending regular, mild pulses of electrical energy to the brain via the vagus nerve. The auricular nerve is connected to the vagus nerve and was found to provide similar physiological response during stimulation.

The concept of auricular nerve stimulation for treatment of epilepsy is described in U.S. Pat. No. 7,797,042. The concept of epilepsy detection during sleep can be found in WO 2001017429. However, a continuing need exists for a system to effectively monitor seizure events and deliver VNS when appropriate.

SUMMARY

The disclosure herein teaches a neuro-stimulation platform and a method of its use. The platform is comprised of one or more nerve stimulation devices and one or more epilepsy seizure detectors which provide synchronized auricular nerve stimulation to reduce or even prevent the occurrence of epileptic seizures during sleep. The device may provide stimulation whenever a seizure is detected and may also provide intermittent activation, including pre-epileptic seizure activation, in order to reduce the number of seizures. The system may be used during sleep or in other parts of a person's daily activity cycle.

The platform consists of the following elements:
a. at least one or more in-ear nerve stimulation devices, activated by a control unit;
b. at least one epilepsy seizure detector.
c. a control unit that triggers the one or more nerve stimulation devices and enables ongoing monitoring of the epileptic condition and treatment. The control unit may be integrated with the seizure detector.

The control unit may include a closed feedback loop controlling the stimulation level in accordance with the seizure signals measured on a real-time basis.

A non-exhaustive list of possible configurations of the seizure detector(s) includes: i. a sensor/detector positioned under the mattress, without direct contact with the patient; ii. a sensor/detector integrated with the stimulation device; and ii. a wrist sensor that measures hand movements.

The disclosure herein also teaches a method for treatment and prevention of epileptic seizures using the system described above in general terms and in greater detail below.

In an aspect of the present invention, there is provided a system for inhibition or treatment of an aberrant neurological event in a subject. The system includes: one or more detectors; a controller; and one or more stimulators of the vagus nerve, wherein the one or more detectors sense signs of a repetitive movement in a subject, and the one or more detectors transmit a signal to the controller indicating possible onset of the repetitive movement. The controller is configured to receive the signal from the one or more detectors to determine if a repetitive movement has occurred, and to provide commands to the one or more stimulators to provide stimulation to the subject when the signal from the one or more detector indicates possible onset of the repetitive movement(s).

In an embodiment of this system, the controller commands the one or more stimulators to provide stimulation after the signal from the one or more detectors exceed a signal frequency threshold, or a signal duration threshold, or a combination thereof.

In another embodiment of the system, the detector is in direct or indirect contact with the subject.

In another embodiment of the system, the degree of stimulation commanded by the controller is dependent on the frequency, the intensity and/or the duration of repetitive movements detected in the subject.

In another embodiment of the system, the one or more stimulators are a plurality of stimulators. In some cases of this embodiment, the controller commands the plurality of stimulators to simultaneously provide stimulation to the subject. In other cases of the embodiment, the controller commands the plurality of stimulators to provide stimulation according to a pre-defined timing pattern.

In another embodiment of the system, the aberrant neurological event is an epileptic or pre-epileptic convulsive seizure.

In a further embodiment of the system, the one or more detectors is selected from the group consisting of a movement detector, EEG sensor, heart rate sensor, breathing sensor, and pressure sensor.

In another embodiment of the system, the one or more detectors is an EEG sensor configured to confirm the onset of an aberrant neurological event.

In yet another embodiment of the system, the repetitive movements is a spasm of one or more movements per three seconds.

In a further embodiment of the system, the controller commands the one or more stimulators to provide stimulation to the subject when the duration of the repetitive movement(s) exceeds a threshold of ten seconds.

In another embodiment of the system, the one or more detectors and the controller are in wired or wireless communication, and wherein the controller and the one or more stimulators are in wired or wireless communication.

In still another embodiment of the system, the intensity and/or the duration of stimulation is adjusted by the controller in response to continuous signals received by the controller from the one or more detectors.

In a further embodiment of the system, the one or more detectors, controller, and one or more stimulators are in separate devices. In other instances they can be integrated into a single device.

In a further embodiment of the system, the at least one stimulator stimulates the auricular branch of the vagus nerve (ABVN) when the one or more stimulators are placed in one or both ears of the subject.

In an embodiment of the system, the controller parameters are configurable within the system or by a configuration device external thereto, and the configuration device is in wired or wireless communication with the controller. In some instances of this embodiment, the configurable controller parameters are one or more of threshold activation level, stimulation frequency, and stimulation amplitude.

In yet another embodiment of the system, the system further includes a communication module that is configured to report system configuration and stimulation data to one or more monitoring devices. In some instances of this embodiment, there is an application in one or more remote devices in wireless communication with the one or more monitoring devices to receive the system configuration and stimulation data.

In yet another embodiment of the system, the system is configured to monitor a subject during a sleeping period.

In another embodiment of the system, the system is configured to monitor a subject during the active, non-sleeping, part of his day.

In a further embodiment of the system, the system further comprises a rechargeable power source.

In another embodiment of the system, the system comprises a closed-loop feedback mechanism to adjust the stimulation level of the system's response to the signal received from the one or more detectors.

In another aspect of the present invention, there is provided a method for treating and preventing epileptic seizures and the onset or pre-onset of epileptic seizures. The method includes the steps of: collecting signals from each of one or more detectors indicating the presence of a repetitive movement; analyzing signals received from the one or more detectors to determine the intensity of the stimulation of the auricular branch of the vagus nerve (ABVN) required to control, to moderate or to prevent current and future repetitive movements; and when required, signaling one or more stimulators to stimulate the ABVN so that the repetitive motion ceases using the determined stimulation intensities.

In an embodiment of the method, the method further includes a step of continuously monitoring the repetitive movements of a patient by the one or more detectors and providing signals therefrom.

In yet another embodiment of the method, the method further includes a step of attaching the one or more stimulators to the ear of a patient.

In still another embodiment of the method, the method further includes a step of providing parameters to a controller to define the minimum duration between seizures and to determine the threshold detector values for amplitude, frequency and duration of repetitive movements and to define amplitude, frequency, and duration for a plurality of stimulation levels of the one or more stimulators.

In another embodiment of the method, the stimulation by the one or more stimulators increases in steps determined by the number of seizures in a single epileptic episode, the episode defined as occurring between two separator durations.

In still another embodiment of the method, the method further includes a step of providing n intensities of stimulation to the one or more stimulators for stimulating the nerve, where $n \geq 2$ and successive intensities increase monotonically with respect to the intensity of its predecessors.

In another embodiment of the method, the method further includes a step of determining whether there is another repetitive movement which has occurred during a predefined separator duration.

In yet another embodiment of the method, the method further includes a step of stimulating the auricular branch of the vagus nerve in one ear.

In still another embodiment of the method, the method further includes a step of stimulating the auricular branch of the vagus nerve in both ears. In some instances of this embodiment, the method further includes a step of stimulating the auricular branch of the vagus nerve in both ears simultaneously. In other instances of this embodiment, the method further includes a step of stimulating the auricular branch of the vagus nerve in both ears, the stimulation alternating between the ears according to a predefined timing schedule.

In yet another embodiment of the method, the stimulation is applied as electrical stimulation and/or as sound stimulation.

The foregoing and other objects, features, and advantages will become more apparent from the following detailed description, which proceeds with reference to the accompanying figures.

DETAILED DESCRIPTION

Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "comprises" means "includes." The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

"Detector" and "sensor" are used synonymously herein.

"Controller" is used synonymously with "control unit".

"Aberrant neurological event" includes spasms, convulsive seizures and absent seizures, except where specifically otherwise limited. Repetitive movement(s), abbreviated herein as rm(s), is deemed to be an aberrant neurological event(s).

Overview of Several Embodiments

Provided herein is a system and method for monitoring a subject that has a neurological disorder. The system provides appropriate treatment by way of vagus nerve stimulation (VNS) upon onset or pre-onset of an aberrant muscular event arising from the neurological disorder. The description of the system herein proceeds with respect to the accompanying figures.

Figure 1:
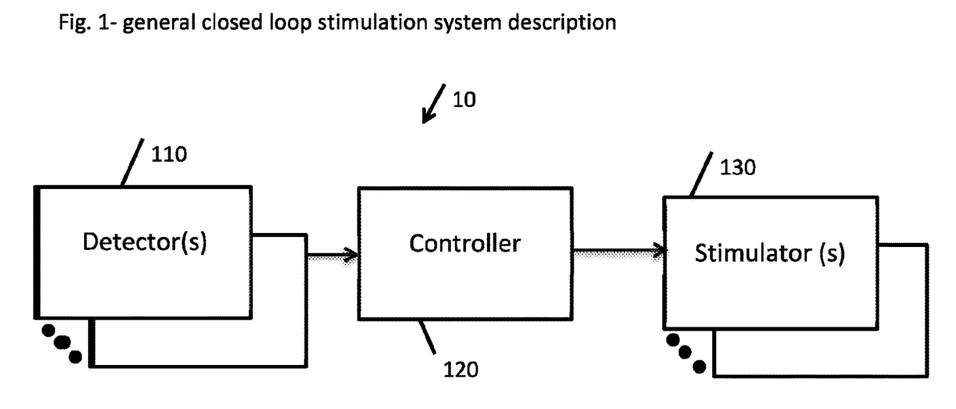
FIG. 1 illustrates a block diagram of a general closed-loop neuro-stimulation system.

FIG. 1, to which reference is now made, depicts a block diagram of the components of the described system. The diagram includes at least one detector 110, which transmits a detection signal to a controller 120, which in turn sends a stimulation command to at least one neuro-stimulator of the vagus nerve 130.

Detectors, also sometimes referred to herein as sensors without any intent at distinguishing between the terms, for detecting epileptic seizures includes spasm detectors selected from, but not limited to, one or more of the following:

Movement detector, wearable by, or remote from, the patient
Movement detector positioned under the mattress, e.g. pressure sensor
EEG sensor
Heart rate sensor
Respiratory sensor Each detector measures one or more signs of spasm and the decision algorithm within the controller requires one or more spasm sign signals received from one or more detectors. For example, differentiating a patient's voluntary intended repetitive movement from neurological disorders resulting in involuntary seizures would require spasm detection by at least both an EEG sensor and a movement detector.

Spasms, as used herein, are defined as repetitive movements (rm) faster than a predetermined frequency, in the range of 0.3 to 15 HZ, typically faster than one movement per second. The spasm may alternatively be predefined as being above a certain intensity (amplitude) and/or greater than a predetermined duration.

Seizure, as used herein, is synonymous with spasm. Seizures can be expressed in muscle spasms, muscle contractions or limb shaking. In the discussion herein, the term "spasm" will often be used for all types of convulsive seizures without intent at distinguishing between the terms "spasm" and seizure". It should be readily understood that non-convulsive epileptic events called "absence seizures" can readily be detected by EEG sensors alone. However since these latter events are much less severe and normally resolve themselves within a few seconds, they may not need stimulation to be brought under control.

A spasm will be deemed as all repetitive movements with the above discussed frequency occurring within a given time period temporally separated from another set of repetitive movements by a predefined duration. The latter is herein defined as a separator duration.

A control unit, also often described herein as a controller, will periodically receive readings from the one or more seizure detectors. It will apply at least one decision algorithm to detect spasm signs using predefined parameters. These will include at least one of the following: threshold values for the spasm signs sensed by the one or more detectors: amplitude, duration and frequency of the signs.

Once a spasm occurs for longer than a set duration, typically between 1 to 30 seconds (more typically 10 seconds, and is detected by the at least one detectors, the control unit activates a VNS stimulator, such as a non-invasive auricular branch vagus nerve (ABVN) stimulator. Each of the one or more electrical stimulators is activated by the control unit at predefined stimulator parameters including intensity (amplitude), and/or frequency and/or duration.

Non-invasive access to the auricular branch of the vagus nerve in some embodiments of this invention is provided by a stimulator and one or more electrodes. These stimulators can generally be a type of stimulation device located behind the ear (BTE), in the ear (ITE), in ear canal (IEC), or completely in ear canal (CIC), or any combination of these. Non-invasive stimulation of the vagus nerve can be performed at other body sites such as the carotid branch of the vagus nerve.

Figure 3A:
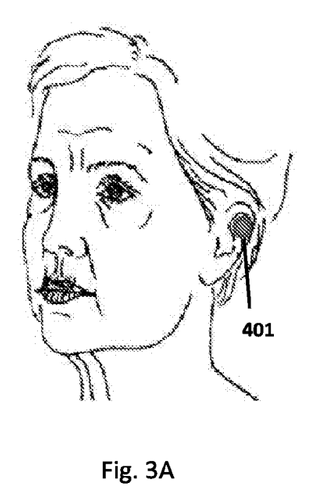
FIG. 3A shows the stimulator of the closed-loop stimulation system positioned in the ear canal or outer ear of a user.

Reference is now made to FIG. 3A, which shows a stimulator (401) which stimulates the auricular nerve and is positioned in the ear canal or in the outer ear.

Electrical stimulation of the vagus nerve can be effected by a wide spectrum of activation means. A specific example for the current disclosure is stimulation of the vagus nerve, particularly the auricular branch of the vagus nerve. In a specific embodiment, such activation is done in an afferent direction, resulting with activation of brain centers that are linked to the vagus nerve. The stimulation can be done using an implanted nerve stimulator and stimulation lead. Another example of electrical nerve stimulation can be done by stimulation of nerves using non-invasive external electrical stimulator. A specific example of such external stimulation is transcutaneous electrical nerve stimulation (TENS) of the auricular branch of the vagus nerve that is located in the ear of the subject.

An additional way to perform non-invasive VNS of the auricular branch is by means of low frequency sound or other vibrations which pass through the ear drum and stimulate the vagus nerve. The low frequency and/or amplitude of the sound or other vibration source may be below the frequency and amplitude audible to humans.

The activation of the one or more neuro-stimulators can be effected with one of the following connection means:

Wired connection between the control unit and the stimulator
Wireless connection between the control unit and the stimulator In some cases, the at least one neuro-stimulation device will be activated as long as the spasm continues.

In some cases, the stimulation parameters for the at least one stimulation device can be changed by the controller during the duration of a prolonged spasm. The closed loop of the system discussed in more detail below can automatically attenuate or amplify the stimulation levels (amplitude, pulse width or frequency) in accordance with the signs detected and signals conveyed to the control unit.

The automatic closed loop neuro-stimulation system monitors the patient constantly to detect spasms/seizures. A spasm may be detected by the system automatically before it starts or shortly after it starts, in reaction to which the control unit of the system activates specific neuro-stimulation by the one or more neuro-stimulator devices. The system monitors the reaction of the patient to the neuro-stimulation after activating the neuro-stimulator(s). The system will adjust the neuro-stimulation according to the reaction of the patient as detected by a special set of dedicated detectors, thereby effectively generating a closed-loop feedback system. The system may shut off the neuro-stimulation shortly after the end of the seizure as sensed by its sensors.

In some cases, immediately upon detection of rapid multiple movements—two or more movements—low intensity stimulation will be applied. If the rapid movements continue after an additional predetermined set time, the stimulation level is increased to a higher level.

Low intensity stimulation, also described herein as low level stimulation, is defined as a level of stimulation that does not cause any sensation or irritation to the patient. High level stimulation is defined as a level that causes sensation or irritation to the patient.

In some cases, more than two stimulation levels may be applied thus allowing a more gradual increase in the stimulation level to the vagus nerve. Additionally, when more than two stimulation levels are used, higher intensity levels of stimulation can be attained.

In some cases, a test is performed to determine a range for low and high levels of stimulation for each individual subject. This is done prior to the start of regular monitoring and treatment of the individual, the results of which are used in configuring the controller for use with the individual subject.

In some embodiments, stimulation elements will be placed only in one ear. In other embodiments, stimulation elements will be placed in both ears. In yet other embodiments, stimulation of both ears is done simultaneously. In still other embodiments, when stimulation is effected in both ears, stimulation is alternated between the two ears in order to reduce nerve exhaustion.

Figure 2:
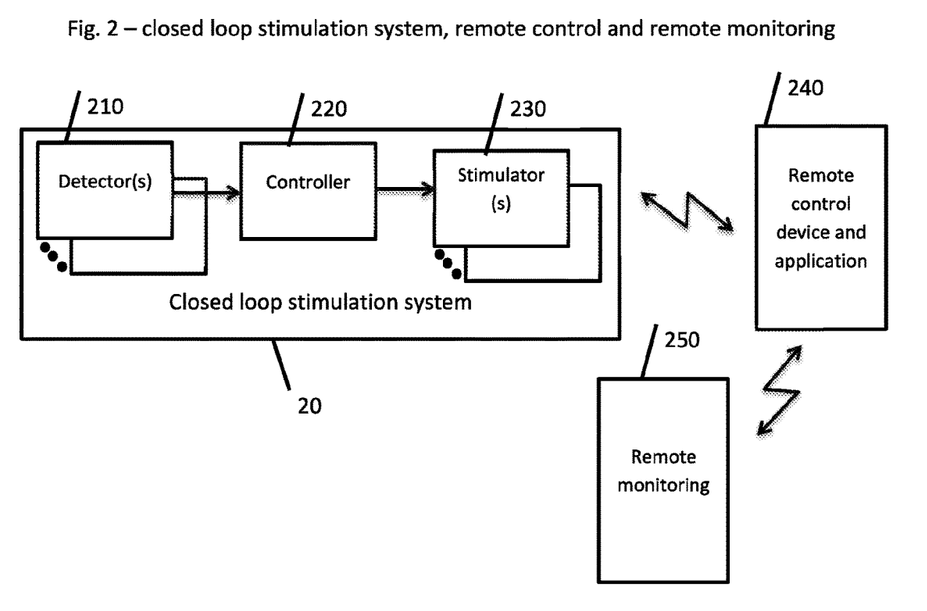
FIG. 2 depicts a block diagram of another embodiment of a closed-loop neuro-stimulation system.

FIG. 2 depicts a block diagram of another embodiment of the components of the closed loop stimulation system 20 described herein. The system includes at least one detector 210, which transmits a detection signal to a controller 220, which in turn transmits a stimulation command to at least one stimulator of the vagus nerve 230. These transmissions may be through wired connections or wireless communications.

In the embodiment of FIG. 2, the closed loop neuro-stimulation system 20 may include a specific application of a smart phone (or other remote control device and application) 240. The application wirelessly communicates with the system 20 to collect information on a seizure alert or to collect information on the set of parameters being used by the system or to collect periodic data.

When a seizure alert is received it may be wirelessly transferred to a local control center for remote monitoring 250. The local control center may use a dedicated application in the phone of a parent or an emergency center which the control center can call for and/or provide assistance. The application may also allow communication with a treatment center to upload the periodic data of the system or to download a new parameter set (detector and/or stimulator parameters) for the system.

In some systems, the detector(s) may be integrated with the control unit, i.e. the controller.

In some systems, there is automatic activation of the at least one stimulator following seizure detection.

Figure 3B:
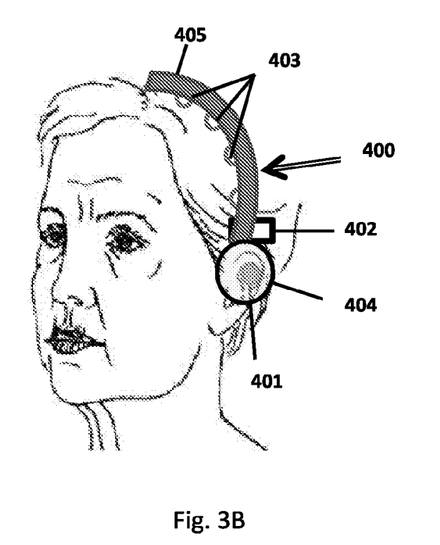
FIG. 3B depicts an embodiment of the stimulation of the auricular/vagal branch through the use of a headphones configuration.

In some systems, there may be a combination of electrical stimulation and sound activation for stopping the seizure. This dual system may be more effective for stopping seizures. An example of the dual system may be found in FIG. 3B where activation can be electrical or through sound using for example an ear phone configuration such as shown in FIG. 3B and discussed immediately below. Other combinations of these two modules may also be designed and used.

FIG. 3B, to which reference is now made, depicts an embodiment of the invention, were the system is integrated with audio headphones. FIG. 3B shows the integration of the stimulator (401) with headphones (400). The headphones includes a control unit (402) which also provides electrical power to the stimulator. The connectivity of control unit (402) to stimulator (401) can be effected through conductive wires or through wireless communication. Such wireless communication can be electrical transmission such as WIFI or Bluetooth or alternatively through magnetic transmission. The magnetic transmission can provide a magnetic field that will generate an inductive current in the stimulator (401). The headphones (400) can also include a plurality of EEG detectors (403) for closed-loop monitoring and control. The plurality of EEG detectors are positioned on a headband (405) of headphones (400).

The headphone (400) includes a transmission element (404) for auricular transmission. The auricular transmission can also transmit acoustic waves at frequencies audible to the human ear that will be delivered separately or together with the electrical stimulation. In some embodiments, the acoustic transmission will be at sound frequencies below the range of human hearing. Such low frequency transmissions are expected to vibrate the ear drum without causing any audible sound. Since the outer side of the ear drum is known to innervate the vagus nerve, it is expected that such vibration will cause vagal stimulation/activation.

In other systems, the patient himself may be able to activate stimulation if he feels a seizure coming on. In other systems, the patient himself may be able to block stimulation if he does not feel a seizure coming on. This could typically be used for false alarms. If the patient feels okay, he may deactivate the stimulation. In other systems, the patient may both activate and block stimulation depending on how he feels.

Figure 4:
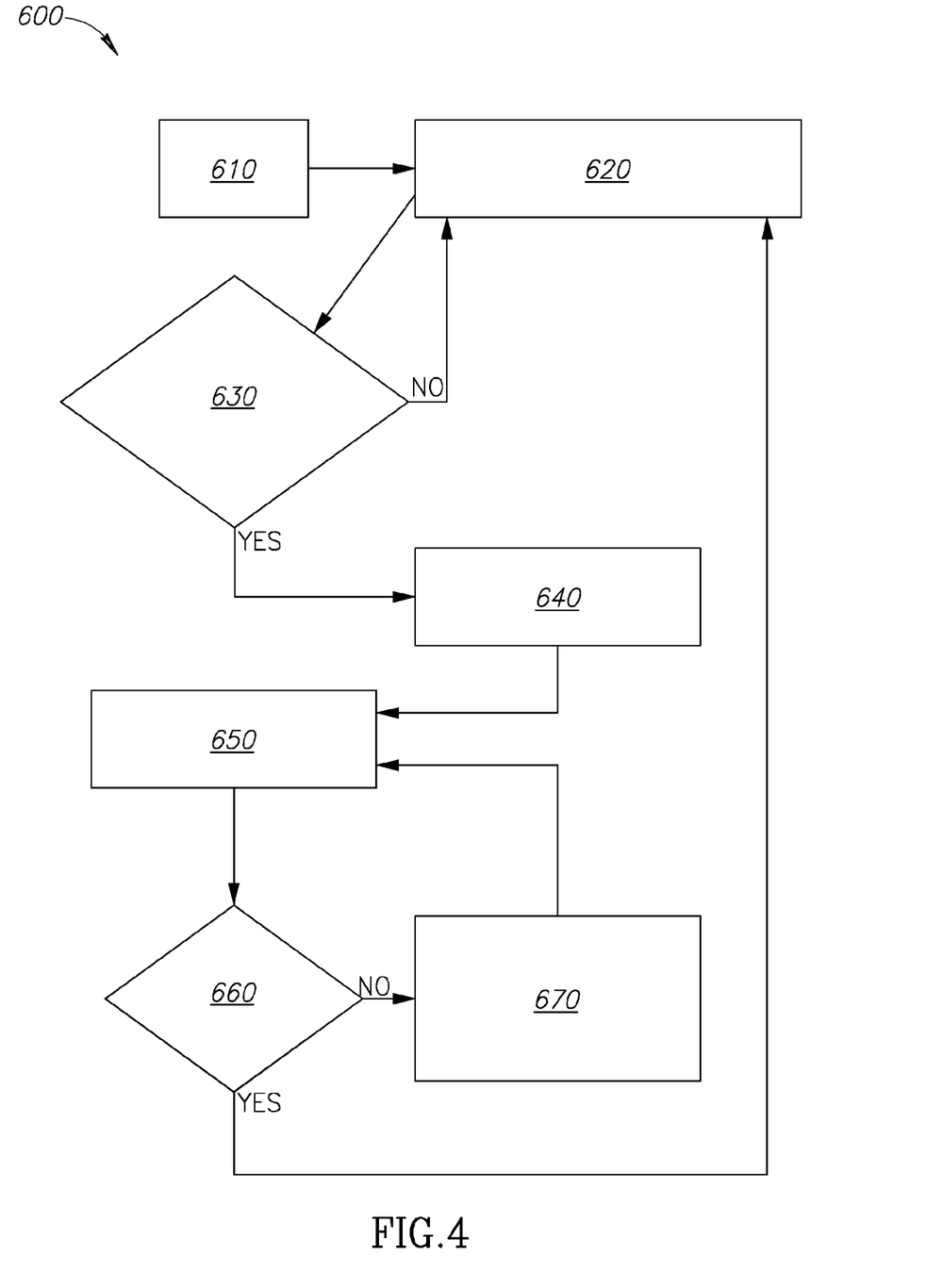
FIG. 4 illustrates a flowchart of a method using the systems in FIG. 1 through 3B.

FIG. 4, depicts a flowchart of the method 600 for closed-loop feedback operation of an illustrative system such as the exemplary systems indicated in FIGS. 1-3B and discussed therewith.

The following are the steps of method 600.

610. Set the parameters of operation.

620. Detector(s) continuously monitors for repetitive movements (rms) or other signs of an epileptic event and sends signals to controller.

630. If rms (or other signs) indicating an epileptic event is identified by the controller based on signals it receives from the detector(s), proceed to the next step, step 640. If no rms are present as determined by the controller, return to step 620.

640. Controller determines the energy level to use to stimulate the vagus nerve and instructs stimulator(s) accordingly.

650. Stimulator(s) stimulates nerve at designated first energy level determined by controller.

660. If detector(s) senses that rms cease for at least the pre-defined separator duration after stimulating at first energy level, controller indicates (step 660) that no further stimulation is required and the system returns to step 620.

670. If detector(s) determines that rms do not cease after stimulation at the first energy level, the controller receives signals from the detector(s) to that effect and instructs the stimulator(s) (step 650) to stimulate at a higher energy level. 680. Repeat steps 650, 660 and 670 at monotonically increasing energy levels until the highest predefined energy level n is reached or until rms cease as discussed also in step 660 and then go to step 620.

The above method represents a closed loop method for using the systems in FIGS. 1 to 3B to treat on-going epileptic seizures and/or to prevent the occurrence of impending epileptic seizures.

In FIG. 4, the parameters that must be entered into the system prior to the system's activation include: the threshold levels of the intensity, and/or the frequency and/or the duration of a signal received from a detector indicating the presence of a spasm of aberrant repetitive movements and the frequency range of the repetitive movements of the aberrant muscular activity; the spasm separator duration used to detect distinct seizures; and the threshold levels of the intensity, and/or the frequency and/or the duration of the stimulation to be provided by the stimulator(s).

The method in FIG. 4 does not explicitly show that the controller checks if the repetitive movements detected occur within a single seizure separated by two predefined seizure separator durations, one before and one after the seizure. That is deemed to be implied in the Figure.

The above description may have a controller configured to increase the intensity of stimulation by the stimulators after each new rm is detected. In other cases, the controller can be configured so that each stimulator stimulates a sequence of two or more rms before having the energy of its stimulation increased. In other cases, the controller may be configured to increase the intensity level of stimulation by the stimulators if one or more of the following exceeds a predefined value: frequency of the rms, duration of the rms, intensity of the rms, and combinations thereof. It should be readily understood by persons skilled in the art that the listing above is not intended to be exhaustive.

It should be noted that while not indicated in FIG. 4, the controller is configured to determine when no rms is detected during the separator duration required to demarcate adjacent rms.

While FIG. 4 shows that the ramping up of the stimulation may be provided by the neuro-stimulators in n steps, it should readily be understood that ramping up of the stimulation provided by the neuro-stimulators can be done in as few as two steps.

Additionally, while not shown in FIG. 4, the described method can be adapted for use with any of the detectors or other features discussed herein with regard to FIGS. 1 and 2. It should also be readily understood that while the observed epileptic characteristic of rms is being monitored in FIG. 4, other measurable features (signs) of epileptic events may also be monitored and used instead of rms to track epileptic activity.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A system for inhibition or treatment of an aberrant neurological event in a subject, comprising:
   at least one detector;
   a controller; and
   at least one stimulator of the vagus nerve,
   wherein the at least one detector senses signs of a repetitive movement in a subject,
   wherein the at least one detector transmits a signal to the controller indicating possible onset of the repetitive movement; and
   wherein the controller is configured to receive the signal from the at least one detector, to determine if a repetitive movement has occurred, and to provide commands to the at least one stimulator to provide stimulation to the subject when the signal from the at least one detector indicates possible onset of the repetitive movement,
   wherein the at least one stimulator stimulates the auricular branch of the vagus nerve (ABVN) when the at least one stimulator is placed in one or both ears of the subject, and
   wherein the at least one stimulator provides stimulation at a low intensity, and if the repetitive movements do not cease, the controller commands the at least one stimulator to provide stimulation at an increased intensity.

2. The system of claim 1, wherein the degree of stimulation commanded by the controller is dependent on the frequency, intensity and/or duration of repetitive movement detected in the subject.

3. The system of claim 1, wherein the at least one stimulator is two or more stimulators.

4. The system of claim 3, wherein the controller commands the plurality of stimulators to provide stimulation according to a pre-defined timing pattern.

5. The system of claim 1, wherein the aberrant neurological event is an epileptic or pre-epileptic convulsive seizure.

6. The system of claim 1, wherein the at least one detector is selected from the group consisting of a movement detector, EEG sensor, heart rate sensor, breathing sensor, and pressure sensor.

7. The system of claim 1, wherein the repetitive movement is a spasm of at least one movement per three seconds.

8. The system of claim 1, wherein the configurable controller parameters is at least one of threshold activation level, stimulation frequency, and stimulation amplitude.

9. The system of claim 1, wherein the system is configured to monitor a subject during a sleeping period.

10. The system of claim 1, wherein the system is configured to monitor a subject during the active, non-sleeping, part of his day.

11. The system of claim 1, wherein the system comprises a closed-loop feedback mechanism to adjust the stimulation level of the system's response to the signal received from the at least one detector.

12. The system of claim 1, wherein the controller commands the at least one stimulator to provide stimulation to the subject when the repetitive movement exceeds a set time threshold.

13. The system of claim 1, wherein the set time threshold is 5-10 seconds.

14. The system of claim 1, wherein the stimulation occurs in both ears simultaneously if the repetitive movements do not cease.

15. A method for treating and preventing epileptic seizures and the onset or pre-onset of epileptic seizures, comprising the steps of:
   collecting signals from each of at least one detector indicating the presence of a repetitive movement;

analyzing signals received from the at least one detector to determine the intensity of the stimulation of the auricular branch of the vagus nerve (ABVN) required to control, moderate or prevent current and future repetitive movements; and when required, signaling at least one stimulator to stimulate the ABVN so that the repetitive motion ceases using the determined stimulation intensities.

16. The method according to claim 15 further comprising a step of continuously monitoring the repetitive movements of a patient by the at least one detector and providing signals therefrom.

17. The method according to claim 15, further including a step of attaching the at least one stimulator to the ear of a patient.

18. The method according to claim 15, further comprising a step of providing parameters to a controller to define the minimum duration between seizures and to determine the threshold detector values for amplitude, frequency and duration of repetitive movement(s) and to define amplitude, frequency, and duration for a plurality of stimulation levels of the at least one stimulator.

19. The method according to claim 15, where stimulation by the at least one stimulator increases in steps determined by the number of seizures in a single epileptic episode, the episode defined as occurring between two separator durations.

20. The method according to claim 15, further comprising a step of stimulating the auricular branch of the vagus nerve in one ear.

21. The method according to claim 15, further comprising a step of stimulating the auricular branch of the vagus nerve in both ears.

22. The method according to claim 21, further comprising a step of stimulating the auricular branch of the vagus nerve in both ears, the stimulation alternating between the ears according to a predefined timing schedule.

23. The method according to claim 15, wherein said stimulation is applied as electrical stimulation and/or as sound stimulation.

* * * * *